United States Patent [19]

Gunjikar

[11] 4,061,733

[45] Dec. 6, 1977

[54] VETERINARY COMPOSITIONS FOR INDUCING ESTRUS IN ANIMALS AND METHOD

[76] Inventor: Narayan Vishwanath Gunjikar, Botawala Building, 21, Sitaladevi Temple Road, Bombay, India, 400016

[21] Appl. No.: 732,778

[22] Filed: Oct. 15, 1976

[51] Int. Cl.² .................... A61K 33/34; A61K 31/135
[52] U.S. Cl. .............................. 424/143; 424/248.58; 424/267; 424/330
[58] Field of Search ................ 424/330, 143, 248, 267

[56] References Cited

PUBLICATIONS

San Karan–Chem. Abst., vol. 80 (1974), p. 55987j.
Ross et al.–Chem. Abst., vol. 79 (1973), pp. 143, 107g.
Snook et al.–Chem. Abst., vol. 80 (1972), p. 388b.

*Primary Examiner*—Sam Rosen
*Attorney, Agent, or Firm*—Hammond & Littell

[57] ABSTRACT

Novel veterinary compositions for inducing estrus in animals comprising an effective amount of a homogeneous mixture of non-toxic, veterinary acceptable acid addition salts of cis-clomiphene and trans-clomiphene in a weight ratio of approximately 3:2 and a carrier and to a method of inducing estrus in animals.

9 Claims, No Drawings

VETERINARY COMPOSITIONS FOR INDUCING ESTRUS IN ANIMALS AND METHOD

STATE OF THE ART

U.S. Pat. No. 2,914,563 describes triphenyl compounds of the formula

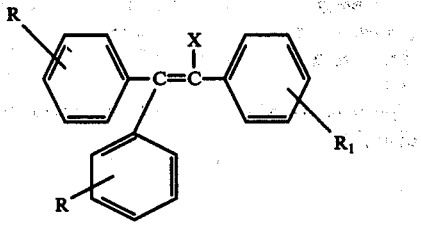

wherein one of the Rs is a basic ether of the formula —$OC_nH_{2n}$—A where n is 2, 3 or 4 and A is a dialkylamino group of 1 to 4 carbon atoms or N-piperidyl or N-morpholinyl and the other R and $R_1$ are hydrogen, halogen or methoxy and X is halogen. The said compounds are stated to have antiestrogenic, anti-inflammatory and gonadotropic activity. Clomiphenes of this type are known for the treatment of inferility and sterility of human beings but they have not been used in veterinary practice or animal husbandry. Initial attempts to use clomiphenes for estrus in animals produced unsatisfactory results.

OBJECTS OF THE INVENTION

It is an object of the invention to provide novel compositions for regulating estrus in animals.

It is another object of the invention to induce estrus in animals.

It is an additional object of the invention to provide a novel process for the preparation of the novel clomiphene mixture.

These and other advantages and objects of the invention will become obvious from the following detailed description.

THE INVENTION

The novel veterinary compositions of the invention for inducing estrus in animals comprises an effective amount of a homogeneous mixture of non-toxic, veterinary acceptable acid addition salts of cis-clomiphene and trans-clomiphene in a weight ratio of approximately 3:2 and a carrier. The compositions are ideal for inducing estrus in all types of farm animals, pets, horses and wild animals.

Examples of suitable acids for the acid addition salts are inorganic acids such as hydrochloric acid, hydrobromic acid, nitric acid, sulfuric acid or phosphoric acid and organic acids such as acetic acid, propionic acid, tartaric acid, citric acid, maleic acid, fumaric acid, succinic acid and alkane sulfonic acids. Particularly preferred is citric acid.

Administration of the compositions to animals has produced the following results: animals who are anoestrus exhibit estrus; animals which exhibit estrus but ovulation is either delayed or absent, exhibit ovulation within forty eight hours, of clomiphenes treatment; treatment in mid estrus period induces ovulatory estrus. Breeding can be done round the year in case of animals with seasonal breeding such as buffaloes, and pets like dogs. In multi parous animals like sheep and pigs, superovulation is induced which radically improves economics. Estrus synchronization can be obtained in specially bred animals such as race horses or prize cattle. Satisfactory results were obtained in sheep breeding programs with the administration of the compositions.

The veterinary compositions may be in the form of tablets, coated tablets, granules, emulsions, syrups, solutions or suspensions and may be added to the drinking water or feed of the animals. The carrier may be any of those normally used such as aqueous or non-aqueous vehicles, starch, sugar, honey, etc. The compositions may contain 0.01 to 95% by weight of the acid addition salt of clomiphene.

The novel method of the invention for inducing estrus in animals comprises administering to the animals an amount sufficient to induce estrus of a homogeneous mixture of non-toxic, veterinary acceptable acid addition salt of cisclomiphene and trans-clomiphene in a weight ratio of approximately 3:2. The mixture may be administered orally or parenterally or any convenient method. The usual effective dose is 1 to 2 mg/kg depending upon the specific animal and the method of administation.

For example, the composition may contain jaggary bolus or honey and be administered orally and satisfactory results were obtained within 2 to 8 days of the administration. Satisfactory results were also obtained within 48 hours when the compositions were administered by drenching. The composition was dissolved in 200 to 300 ml of water and was administered with a drenching bottle. For ruminants, 30 ml of a 1% copper sulfate solution was administered before the drenching to close the esophagal groove by chemical reflex and after 2 minutes, the clomiphene citrate was administered by trituration.

The clomiphene acid addition salt composition acts on the hypothalamo-pituitary axis to release $G_n$ RH, which stimulates the anterior pituitary to secrete lutenising hormone and follice stimulating hormone. The composition also has a regulatory effect on the peripheral circulation of estrogens and hence pin-point ovulation takes place.

The novel process of the invention to prepare the novel mixture of the invention comprises dissolving an acid addition salt of clomiphene in an organic solvent, fractionally crystallizing the cis clomiphene salt and the trans clomiphene salt to recover the salts separately and then mixing the salts in a weight ratio of 3 parts of cis-clomiphene salt to 2 parts of trans-clomiphene salt.

To prepare the cis-clomiphene-trans-clomiphene mixture, clomiphene citrate was dissolved in carbon disulfide and the resulting solution was refluxed at 60° C in a reflux condenser during which fractional crystallization occured. The crystal crops of cis-clomiphene citrate and trans-clomiphene citrate were separately collected and then the two salts were admixed to obtain a weight ratio of 3 parts of cis-clomiphene citrate to 2 parts of trans-clomiphene citrate as determined by the absorption curves on a Perkin-Elmer infrared spectrophotometer.

Various modification of the process and compositions of the invention may be made without departing from the spirit thereof and it is to be understood that the invention is to be limited only as defined in the appended claims.

I claim:

1. A veterinary composition for inducing estrus in animals comprising an estrus effective amount of a homogeneous mixture of non-toxic, veterinary acceptable acid addition salts of cis-clomiphene and trans-clomiphene in a weight ratio of approximately 3:2 and a carrier.

2. The composition of claim 1 wherein the salt is the citrate salt.

3. The composition of claim 1 to be taken orally wherein the carrier is honey or jaggary bolus.

4. A method of inducing estrus in animals comprising administering to animals an amount effective to induce estrus of a homogeneous mixture of acid addition salts of cis-clomiphene and trans-clomiphene in a weight ratio of approximately 3:2.

5. The method of claim 4 wherein the acid addition salts is the citrate.

6. The method of claim 4 wherein the homogenous mixture is orally administered after drenching with a 1% copper sulfate solution.

7. A process for the preparation of an estrus inducing composition comprising dissolving an acid addition salt of clomiphene in an organic solvent, fractionally crystallizing the cis-clomiphene salt and the trans-clomiphene salt to recover the salts separately and mixing the salts in a weight ratio of 3 parts of cis-clomiphene salt and 2 parts of trans-clomiphene salt.

8. The process of claim 7 wherein the salt is the citrate salt.

9. The process of claim 7 wherein the solvent is carbon disulfide.

* * * * *